United States Patent
Horvath et al.

(10) Patent No.: US 8,680,412 B2
(45) Date of Patent: Mar. 25, 2014

(54) FOOTSWITCH OPERABLE TO CONTROL A SURGICAL SYSTEM

(75) Inventors: Christopher Horvath, Irvine, CA (US); Mark Buczek, Oceanside, CA (US); T. Scott Rowe, Dana Point, CA (US)

(73) Assignee: Novartis AG, Basel (CH)

(*) Notice: Subject to any disclaimer, the term of this patent is extended or adjusted under 35 U.S.C. 154(b) by 398 days.

(21) Appl. No.: 12/836,961

(22) Filed: Jul. 15, 2010

(65) Prior Publication Data
US 2011/0106068 A1    May 5, 2011

Related U.S. Application Data

(62) Division of application No. 11/389,808, filed on Mar. 27, 2006, now Pat. No. 7,781,941.

(60) Provisional application No. 60/667,290, filed on Mar. 31, 2005.

(51) Int. Cl.
*H01H 3/14* (2006.01)
*H01L 41/113* (2006.01)

(52) U.S. Cl.
USPC .......................... 200/86.5; 310/339; 307/113

(58) Field of Classification Search
USPC ............ 310/319, 338, 339; 74/514; 200/86.5, 200/52 R; 307/113
See application file for complete search history.

(56) References Cited

U.S. PATENT DOCUMENTS

| | | | |
|---|---|---|---|
| 2,986,953 A | 6/1961 | De Armond et al. | |
| 3,761,598 A | 9/1973 | Haile | |
| 3,789,836 A | 2/1974 | Girten | |
| 3,841,172 A | 10/1974 | Pilch | |
| 3,930,431 A | 1/1976 | Magadini | |

(Continued)

FOREIGN PATENT DOCUMENTS

| DE | 39 03 401 A | 8/1990 |
|---|---|---|
| DE | 3917876 | 12/1990 |

(Continued)

OTHER PUBLICATIONS

Partial European Search Report for Application No. 06111409.6, Publication No. EP1714617, Dated Jul. 5, 2006, Published Oct. 25, 2006, 5 pages.

(Continued)

*Primary Examiner* — Thomas M Dougherty
(74) *Attorney, Agent, or Firm* — Darien Reddick

(57) ABSTRACT

The present invention provides a surgical footswitch that includes a base, a pedal, an encoder assembly, a wireless interface, and an internal power generator. The pedal mounts upon the base and pivots. The encoder assembly couples to the pedal. As the pedal pivots, the encoder assembly translates the mechanical signal of the pedal into a control signal based on the pedals position and/or orientation. The wireless interface couples the encoder assembly to receive the control signal. The wireless interface also couples the surgical footswitch to a surgical console operable to control and direct surgical equipment. The wireless interface passes the control signal from the encoder to the surgical console, which then directs the surgical equipment based on the control signal. This wireless interface eliminates the tangle of wires or tethers, which may be a hazard in the surgical theater. The internal power generator translates footswitch movement into stored energy to eliminate potential failures of the footswitch during a procedure and overcome the need to replace batteries within the footswitch.

9 Claims, 7 Drawing Sheets

(56) References Cited

U.S. PATENT DOCUMENTS

| | | |
|---|---|---|
| 3,980,849 A | 9/1976 | Straihammer |
| 4,168,707 A | 9/1979 | Douvas et al. |
| 4,172,217 A | 10/1979 | Miller |
| 4,202,037 A | 5/1980 | Glaser et al. |
| 4,267,414 A | 5/1981 | Brueggeman |
| 4,274,411 A | 6/1981 | Dotson, Jr. |
| 4,337,939 A | 7/1982 | Hoyle et al. |
| 4,383,167 A | 5/1983 | Gmeinder et al. |
| 4,544,243 A | 10/1985 | Munnerlyn |
| 4,652,215 A | 3/1987 | Kuroyanagi et al. |
| 4,833,306 A | 5/1989 | Milbrett |
| 4,837,857 A | 6/1989 | Scheller et al. |
| 4,844,259 A | 7/1989 | Glowczewskie et al. |
| 4,870,964 A | 10/1989 | Bailey, Jr. et al. |
| 4,871,336 A | 10/1989 | Scheurer |
| 4,901,454 A | 2/1990 | Walkhoff |
| 4,907,589 A | 3/1990 | Cosman |
| 4,965,417 A | 10/1990 | Massie |
| 4,977,811 A | 12/1990 | Suzuki et al. |
| 4,983,901 A | 1/1991 | Lehmer |
| 5,028,802 A | 7/1991 | Webb et al. |
| 5,048,870 A | 9/1991 | Mangini et al. |
| 5,091,656 A | 2/1992 | Gahn |
| 5,094,226 A | 3/1992 | Medcalf et al. |
| 5,157,603 A | 10/1992 | Scheller et al. |
| 5,180,925 A | 1/1993 | Lieb |
| 5,206,672 A | 4/1993 | Rowe |
| 5,237,891 A | 8/1993 | Lundberg et al. |
| 5,268,624 A | 12/1993 | Zanger |
| 5,283,943 A | 2/1994 | Aguayo et al. |
| 5,303,085 A | 4/1994 | Rallison |
| 5,308,355 A | 5/1994 | Dybbs |
| 5,324,900 A | 6/1994 | Gonser et al. |
| 5,342,293 A | 8/1994 | Zanger |
| 5,403,276 A | 4/1995 | Schechter et al. |
| 5,408,076 A | 4/1995 | Griffanti |
| 5,422,521 A | 6/1995 | Neer et al. |
| 5,423,231 A | 6/1995 | Helfrich et al. |
| 5,450,143 A | 9/1995 | Rowe et al. |
| 5,455,766 A | 10/1995 | Scheller et al. |
| 5,488,223 A | 1/1996 | Austin et al. |
| 5,535,642 A | 7/1996 | Moll |
| 5,545,160 A | 8/1996 | O'Rourke |
| 5,549,597 A | 8/1996 | Shimmick et al. |
| 5,554,894 A | 9/1996 | Sepielli |
| 5,580,347 A | 12/1996 | Reimels |
| 5,619,377 A | 4/1997 | Rallison |
| 5,635,777 A | 6/1997 | Telymonde |
| 5,642,227 A | 6/1997 | Rallison |
| 5,662,006 A | 9/1997 | Angeltun |
| 5,673,151 A | 9/1997 | Rallison |
| 5,674,923 A | 10/1997 | Subbaraman et al. |
| 5,724,244 A | 3/1998 | Yabuki |
| 5,787,760 A | 8/1998 | Thorlakson |
| 5,810,765 A | 9/1998 | Oda |
| 5,825,982 A | 10/1998 | Wright et al. |
| 5,842,173 A | 11/1998 | Strum et al. |
| 5,845,264 A | 12/1998 | Nellhaus |
| 5,899,674 A | 5/1999 | Jung et al. |
| 5,910,110 A | 6/1999 | Bastable |
| 5,969,791 A | 10/1999 | Rowe |
| 5,983,749 A | 11/1999 | Holtorf |
| 5,990,400 A | 11/1999 | Hoshino |
| 5,991,087 A | 11/1999 | Rallison |
| 5,996,889 A | 12/1999 | Fuchs et al. |
| 5,997,528 A | 12/1999 | Bisch et al. |
| 6,005,482 A | 12/1999 | Moran et al. |
| 6,010,496 A | 1/2000 | Appelbaum et al. |
| 6,030,290 A | 2/2000 | Powell et al. |
| 6,036,458 A | 3/2000 | Cole et al. |
| 6,039,565 A | 3/2000 | Chou et al. |
| 6,055,458 A | 4/2000 | Cochran et al. |
| 6,059,544 A | 5/2000 | Jung et al. |
| 6,066,129 A | 5/2000 | Larson |
| 6,078,681 A | 6/2000 | Silver |
| 6,087,941 A | 7/2000 | Ferraz |
| 6,098,892 A | 8/2000 | Peoples, Jr. |
| 6,099,521 A | 8/2000 | Shadduck |
| 6,106,512 A | 8/2000 | Cochran et al. |
| 6,117,126 A | 9/2000 | Appelbaum et al. |
| 6,149,621 A | 11/2000 | Makihara |
| 6,149,643 A | 11/2000 | Herekar et al. |
| 6,150,623 A | 11/2000 | Chen |
| 6,155,975 A | 12/2000 | Urich et al. |
| 6,159,205 A | 12/2000 | Herekar et al. |
| 6,179,829 B1 | 1/2001 | Bisch |
| 6,193,710 B1 | 2/2001 | Lemberg |
| 6,204,491 B1 | 3/2001 | Montani |
| 6,238,623 B1 | 5/2001 | Amhof et al. |
| 6,251,113 B1 | 6/2001 | Appelbaum et al. |
| 6,341,726 B1 | 1/2002 | Castanedo et al. |
| 6,360,630 B2 | 3/2002 | Holtorf |
| 6,394,999 B1 | 5/2002 | Williams et al. |
| 6,452,120 B1 | 9/2002 | Chen |
| 6,452,123 B1 | 9/2002 | Chen |
| 6,485,413 B1 | 11/2002 | Boppart et al. |
| 6,491,686 B2 | 12/2002 | Lemberg |
| 6,506,050 B1 | 1/2003 | Steddin |
| 6,512,530 B1 | 1/2003 | Rzepkowski et al. |
| 6,514,268 B2 | 2/2003 | Finlay et al. |
| 6,536,300 B1 | 3/2003 | Gonring |
| 6,583,796 B2 | 6/2003 | Jamar et al. |
| D478,323 S | 8/2003 | Peterson et al. |
| 6,602,185 B1 | 8/2003 | Uchikubo |
| 6,623,429 B2 | 9/2003 | Percival et al. |
| 6,639,332 B2 | 10/2003 | Metzler et al. |
| 6,641,039 B2 | 11/2003 | Southard |
| 6,648,223 B2 | 11/2003 | Boukhny et al. |
| 6,659,998 B2 | 12/2003 | DeHoogh et al. |
| 6,669,340 B2 | 12/2003 | Percival et al. |
| 6,671,535 B1 | 12/2003 | McNichols et al. |
| 6,674,030 B2 | 1/2004 | Chen et al. |
| 6,689,975 B2 * | 2/2004 | Metzler et al. ............... 200/86.5 |
| 6,726,625 B2 | 4/2004 | Luce |
| 6,742,286 B2 | 6/2004 | Giovale |
| 6,743,245 B2 | 6/2004 | Lobdell |
| 6,749,302 B2 | 6/2004 | Percival et al. |
| 6,751,473 B1 | 6/2004 | Goyal et al. |
| 6,783,523 B2 | 8/2004 | Qin et al. |
| 6,784,388 B1 | 8/2004 | Braaten |
| 6,786,602 B2 | 9/2004 | Abitbol |
| 6,816,316 B2 | 11/2004 | Caudle et al. |
| 6,862,951 B2 | 3/2005 | Peterson et al. |
| 6,893,261 B1 | 5/2005 | Feine |
| 6,908,196 B2 | 6/2005 | Herekar et al. |
| 6,945,650 B2 | 9/2005 | Beverly |
| 6,962,094 B2 | 11/2005 | Porter et al. |
| 6,962,581 B2 | 11/2005 | Thoe |
| 7,001,018 B1 | 2/2006 | Martin |
| 7,012,203 B2 | 3/2006 | Hanson et al. |
| 7,019,234 B1 | 3/2006 | Mezhinsky et al. |
| 7,084,364 B2 | 8/2006 | Mezhinsky |
| 7,185,555 B2 | 3/2007 | Peterson et al. |
| 7,193,169 B2 | 3/2007 | Mezhinsky et al. |
| 7,259,340 B2 | 8/2007 | Blaha et al. |
| 7,323,646 B2 | 1/2008 | Braaten |
| 7,381,917 B2 | 6/2008 | Dacquay et al. |
| 7,400,752 B2 | 7/2008 | Zacharias |
| 7,422,432 B2 | 9/2008 | Warner |
| 7,422,582 B2 | 9/2008 | Malackowski et al. |
| 7,439,463 B2 | 10/2008 | Brenner et al. |
| 7,476,799 B2 | 1/2009 | Purchon et al. |
| 7,568,619 B2 | 8/2009 | Todd et al. |
| 7,619,171 B2 | 11/2009 | Horvath et al. |
| 7,708,404 B2 | 5/2010 | Gaida et al. |
| 2001/0006818 A1 | 7/2001 | Amhof et al. |
| 2001/0020401 A1 | 9/2001 | Holtorf |
| 2002/0045887 A1 | 4/2002 | DeHoogh et al. |
| 2002/0047990 A1 | 4/2002 | Ferguson et al. |
| 2002/0115917 A1 | 8/2002 | Honda et al. |
| 2003/0047434 A1 | 3/2003 | Hanson et al. |
| 2003/0073980 A1 | 4/2003 | Finlay et al. |
| 2003/0111327 A1 * | 6/2003 | Metzler et al. ............... 200/86.5 |
| 2003/0132092 A1 | 7/2003 | Metzler et al. |

(56) References Cited

U.S. PATENT DOCUMENTS

| | | |
|---|---|---|
| 2003/0213333 A1 | 11/2003 | McVicar |
| 2004/0024384 A1 | 2/2004 | Novak |
| 2004/0030367 A1 | 2/2004 | Yamaki et al. |
| 2004/0102799 A1 | 5/2004 | Perez et al. |
| 2004/0106915 A1 | 6/2004 | Thoe |
| 2004/0115591 A1 | 6/2004 | Warner |
| 2005/0080403 A1* | 4/2005 | Takahashi ............ 606/1 |
| 2005/0277913 A1 | 12/2005 | McCary |
| 2006/0043179 A1 | 3/2006 | Nycz et al. |
| 2006/0114175 A1 | 6/2006 | Boukhny |
| 2006/0116667 A1 | 6/2006 | Hamel et al. |
| 2006/0145540 A1 | 7/2006 | Mezhinsky |
| 2006/0149418 A1 | 7/2006 | Anvari |
| 2006/0219049 A1 | 10/2006 | Horvath et al. |
| 2006/0236242 A1 | 10/2006 | Boukhny et al. |
| 2006/0247659 A1 | 11/2006 | Moeller et al. |
| 2006/0270913 A1 | 11/2006 | Todd |
| 2007/0008624 A1 | 1/2007 | Hirayama |
| 2007/0081078 A1 | 4/2007 | Cummings et al. |
| 2007/0135866 A1 | 6/2007 | Baker et al. |
| 2007/0146130 A1 | 6/2007 | Hannemann et al. |
| 2007/0152508 A1 | 7/2007 | Mezhinsky |
| 2008/0060662 A1 | 3/2008 | Oh et al. |
| 2008/0085499 A1 | 4/2008 | Horvath |
| 2008/0086117 A1* | 4/2008 | Cao ............ 606/10 |
| 2008/0089277 A1 | 4/2008 | Alexander et al. |
| 2008/0140158 A1* | 6/2008 | Hamel et al. ............ 607/60 |
| 2008/0161783 A1* | 7/2008 | Cao ............ 606/10 |
| 2008/0243105 A1* | 10/2008 | Horvath ............ 606/1 |
| 2008/0243142 A1 | 10/2008 | Gildenberg |
| 2008/0281301 A1 | 11/2008 | Deboer et al. |
| 2009/0049397 A1 | 2/2009 | Boukhny |
| 2009/0121865 A1 | 5/2009 | Hamel et al. |
| 2009/0125337 A1 | 5/2009 | Abri |
| 2009/0300507 A1 | 12/2009 | Raghavan et al. |
| 2009/0303315 A1 | 12/2009 | Charlesworth |

FOREIGN PATENT DOCUMENTS

| | | | |
|---|---|---|---|
| DE | 19509680 A1 | 9/1996 | |
| DE | 20100591 U1 | 6/2001 | |
| DE | 20105851 | 10/2001 | |
| DE | 10033680 A1 | 1/2002 | |
| DE | 10104162 A1 | 8/2002 | |
| DE | 10245591 A1 * | 4/2004 | ............ A61B 19/00 |
| DE | 10245591 | 4/2005 | |
| DE | 102005010094 | 9/2006 | |
| EP | 550124 A2 | 7/1993 | |
| EP | 0630820 | 12/1994 | |
| EP | 0656612 A1 | 6/1995 | |
| EP | 0789929 | 7/2002 | |
| EP | 1394828 | 3/2004 | |
| EP | 1498082 A1 | 1/2005 | |
| EP | 1714617 | 10/2006 | |
| FR | 2646545 | 11/1990 | |
| GB | 1 051 785 A | 12/1966 | |
| GB | 1063067 | 3/1967 | |
| JP | 56-012464 | 7/1954 | |
| JP | 02-193658 | 7/1990 | |
| JP | 6-142105 | 5/1994 | |
| JP | 07-103130 | 4/1995 | |
| JP | 8-56026 | 2/1996 | |
| JP | 8-71085 | 3/1996 | |
| JP | 9-173351 | 7/1997 | |
| JP | 09-205291 A | 8/1997 | |
| JP | 2000-107197 | 4/2000 | |
| JP | 2000 217836 | 8/2000 | |
| JP | 2000-229102 | 8/2000 | |
| JP | 2001-17459 | 1/2001 | |
| JP | 2003-314437 | 11/2003 | |
| JP | 2004-030563 | 4/2004 | |
| JP | 2004-537367 | 12/2004 | |
| WO | WO 96/13845 | 5/1996 | |
| WO | WO 98/08442 | 3/1998 | |
| WO | WO 99/017818 | 10/1998 | |
| WO | WO 99/14648 | 3/1999 | |
| WO | WO 00/12037 | 3/2000 | |
| WO | WO 0186369 | 11/2001 | |
| WO | WO 02/01310 | 1/2002 | |
| WO | WO 02/32354 A1 | 4/2002 | |
| WO | WO 03/053293 | 7/2003 | |
| WO | WO 03/053294 | 7/2003 | |
| WO | WO 2004/019751 | 3/2004 | |
| WO | 2004/030563 | 4/2004 | |
| WO | WO 2005/084570 A1 | 9/2005 | |
| WO | WO 2006/026289 A1 | 3/2006 | |
| WO | WO 2006/060423 | 6/2006 | |
| WO | WO 2007/005507 | 1/2007 | |
| WO | WO/2007/005507 * | 1/2007 | |
| WO | WO 2008/131362 A2 | 10/2008 | |
| WO | WO 2009/023408 A1 | 2/2009 | |

OTHER PUBLICATIONS

Extended European Search Report for Application No. 06111409.6, Publication No. EP1714617, Dated Sep. 8, 2006, Published Oct. 25, 2006, 14 pages.

Written Opinion of the International Search Authority, International Application No. PCT/US08/70715, Jan. 12, 2009, 6 pages.

International Search Report for PCT/US2003/04310, Publication No. WO03081379, 1 page, dated Sep. 23, 2003.

International Search Report for PCT/US2009/046229, Publication No. WO2009/149244, 6 pages, dated Jan. 19, 2010.

International Search Report and Written Opinion for PCT/US2006/25336, Publication No. WO2007/005507, dated Jan. 26, 2007, 8 pages.

Search Report of R.O.C. for Application No. 095123616, Filing Date Jun. 29, 2006, Completed Dec. 20, 2011.

European Search Report for Application No. 06785823.3, Publication No. EP1787105, Published Mar. 12, 2008, dated Jun. 5, 2009, 4 pages.

* cited by examiner

FOOTSWITCH OPERABLE TO CONTROL A SURGICAL SYSTEM

CROSS-REFERENCE TO RELATED APPLICATIONS

This application claims priority under 35 U.S.C. §119 to U.S. Provisional Patent Application No. 60/667,290, filed Mar. 31, 2005, the entire contents of which are incorporated herein by reference. This application is also a divisional application of and claims priority to U.S. patent application Ser. No. 11/389,808 filed Mar. 27, 2006 now U.S. Pat. No. 7,781,941, the entire contents of which are incorporated herein by reference.

TECHNICAL FIELD OF THE INVENTION

The present invention relates generally to systems and methods for controlling a surgical system, and more particularly, to a surgical footswitch operable to securely, reliably, and wirelessly control a complex surgical system.

BACKGROUND OF THE INVENTION

During the use of a complex patient treatment apparatus or surgical system, for example, surgical equipment used when performing ophthalmic surgery, the control of a variety of different subsystems, such as pneumatic and electronically driven subsystems may be required. Typically, the operation of the subsystems is controlled by a microprocessor-driven console. The microprocessor controls within a surgical console receive mechanical inputs from either the operator of the surgical system or from an assistant. A control input device, such as a footswitch, is often used to accept mechanical inputs. These mechanical inputs originate from the movement of the foot of an operator to govern the operation of a subsystem within the patient treatment apparatus. The mechanical inputs from the movement of the foot of the operator are translated into electrical signals which are fed to the microprocessor controls. The electrical signals are then used to control the operational characteristics of a subsystem in a complex patient treatment apparatus.

Examples of footswitches that are designed for receiving mechanical inputs from the movement of the foot of an operator of a complex patient treatment apparatus may be found in several U.S. patents, including U.S. Pat. Nos. 4,837,857 (Scheller, et al.), 4,965,417 (Massie), 4,983,901 (Lehmer), 5,091,656 (Gahn), 5,268,624 (Zanger), 5,554,894 (Sepielli), 5,580,347 5 (Reimels), 5,635,777 (Telymonde, et al), 5,787,760 (Thorlakson), 5,983,749 (Holtorf), and 6,179,829 B1 (Bisch, et al), and in International Patent Application Publication Nos. WO 98/08442 (Bisch, et al.), WO 00/12037 (Chen), and WO 02/01310 (Chen). These patents and patent applications focus primarily on footswitches that include a foot pedal or tillable treadle similar to the accelerator pedal used to govern the speed of an automobile. The movement of the foot pedal or tillable treadle typically provides a linear control input. Such linear control inputs may be used, for example, for regulating vacuum, rotational speed, power, or reciprocal motion.

In more complex footswitch assemblies, side or wing switches may be added to housings on either side of the foot pedal in order to provide additional capabilities to the footswitch. The condition of these side or wing switches is changed by the application of pressure from the front portion of the operator's foot or from the rear portion of the operator's foot.

As these footswitches become more complex, the need to establish secure reliable communications between the footswitch and the surgical console has resulted in a number of wired pathways that connect the footswitch and surgical console. As the footswitches are moved about the operating room, these tethers, wires and cables can become tangled with other equipment. Accidentally disconnecting these cables can result in improper control inputs that have the potential to injure a patient. Therefore a need exists for a reliable footswitch operable to communicate with the surgical system while avoiding the potential hazardous or restrictive environment created by entangled cables.

SUMMARY OF THE INVENTION

The present invention provides a surgical footswitch used to control surgical equipment that substantial addresses the above-identified needs as well as others.

One embodiment provides a surgical footswitch having a base, a pedal, an encoder assembly, and a wireless interface. The pedal mounts upon the base and pivots. The encoder assembly couples to the pedal. As the pedal pivots, the encoder assembly translates the mechanical signal of the pedal into a control signal based on the pedal's position and/or orientation. The wireless interface couples the encoder assembly to receive the control signal. The wireless interface also couples the surgical footswitch to a surgical console operable to control and direct surgical equipment. The wireless interface passes the control signal from the encoder to the surgical console, which then directs the surgical equipment based on the control signal. This wireless interface eliminates the tangle of wires or tethers, which may be a hazard in the surgical theater.

Another embodiment further includes an internal power generator operable to translate footswitch movement into stored energy. This may eliminate a potential failure of the footswitch during a procedure and overcome the need to replace batteries within the footswitch as the surgical footswitch can generate its own power. There are many different ways to derive power from the movement of the surgical footswitch. These include but should not be limited to the piezoelectric effect, inductive power generation, compressing and storing air, mechanical flywheels or other like means known to those having skill in the art.

Another embodiment provides a surgical footswitch having a base, a pedal, an encoder, a motion detector, and a wireless interface. This embodiment extends the capability of existing surgical footswitches wherein the motion detector assembly may be worn by a user and transmit motion information to the surgical footswitch. The encoder assembly may generate additional control signals based on the received motion information. The motion detector may generate motion information based on relative positioning information, on an acceleration sensor used to determine the motion detector assembly's position through integration, on radio triangulation or on other like methods known to those having skill in the art.

Yet another embodiment provides a dual switch surgical footswitch operable to ramp and fire a surgical laser. This dual switch surgical footswitch includes a base, pedal, first switch, second switch, encoder assembly, and interface. The pedal is mounted to the base and operable to pivot about a plane associated with the base. The first switch couples to the pedal and is activated as the pedal orients past the first predetermined point when the pedal is initially depressed. When the first switch is activated a first control signal initializes the laser within the surgical system. The second switch also operably couples to the pedal and is activated when the pedal orients past a second predetermined point such as reaching the bottom of the range of motion. This second control signal directs the firing of the ramped laser. The trigger time between the activation of the first switch and the second switch allows stress on the laser to be relieved by allowing the laser to be ramped to power.

An encoder assembly coupled to the pedal may be operable to produce a third control signal based on the pedal's position and for orientation. The interface couples to the encoder and establishes a communication path between the surgical footswitch and the surgical console. This surgical console is operable to control or direct the surgical equipment based on the control signals.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGs., like numerals being used to refer to like and corresponding parts of the various drawings.

Figure 1:
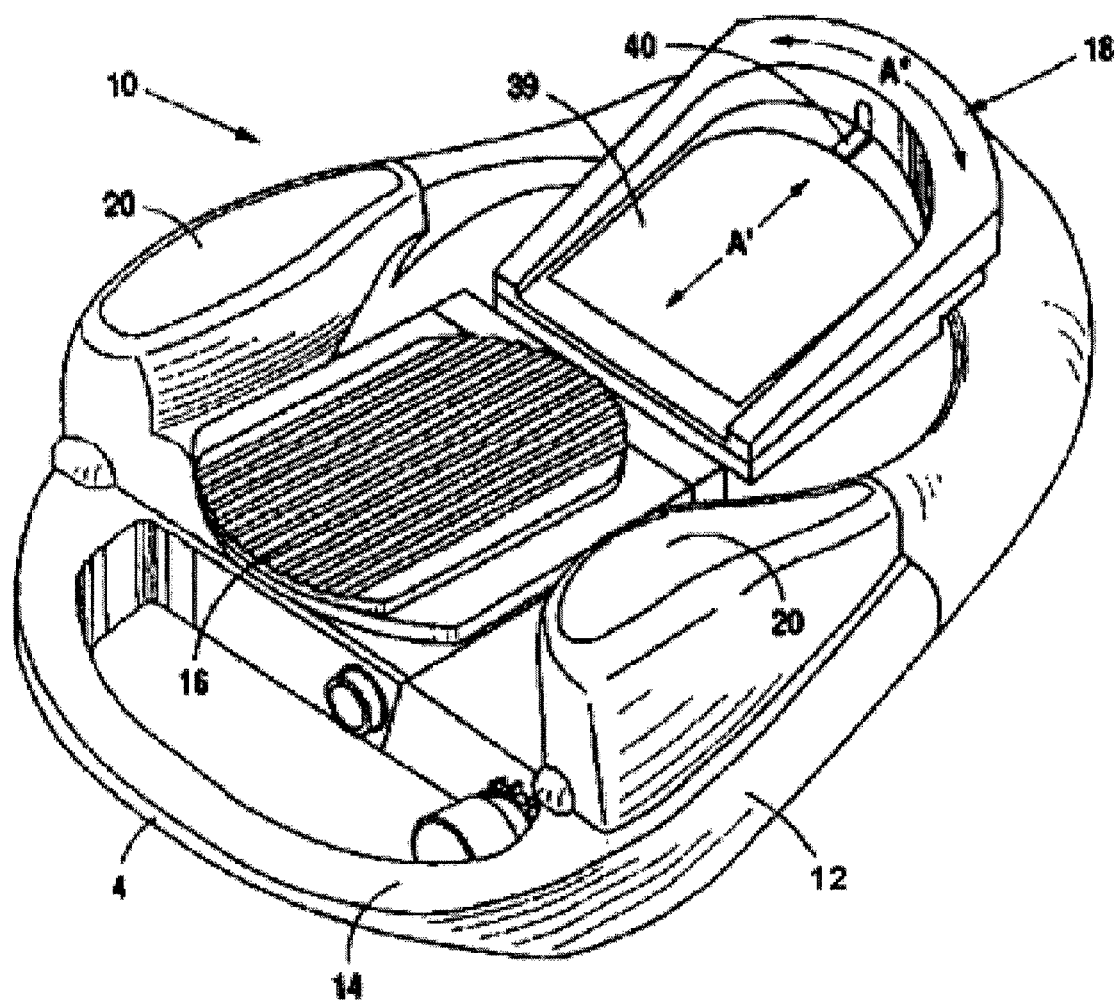
FIG. 1 depicts an embodiment of a footswitch assembly in accordance with an embodiment of the present invention.

FIG. 1 depicts an embodiment of a footswitch assembly 10. The surgical footswitch assembly 10 includes a body or housing that further includes bottom housing 12 and top housing 14, and a foot pedal or treadle 16, all of which can be made from any suitable material, such as stainless steel, titanium or plastic. Other embodiments may additionally include a separate heel cup assembly 18 and a handle 4 positioned in the front. Side or wing switches 20 may be placed on the top of housing 14 on either side of the foot pedal 16.

Figure 2:
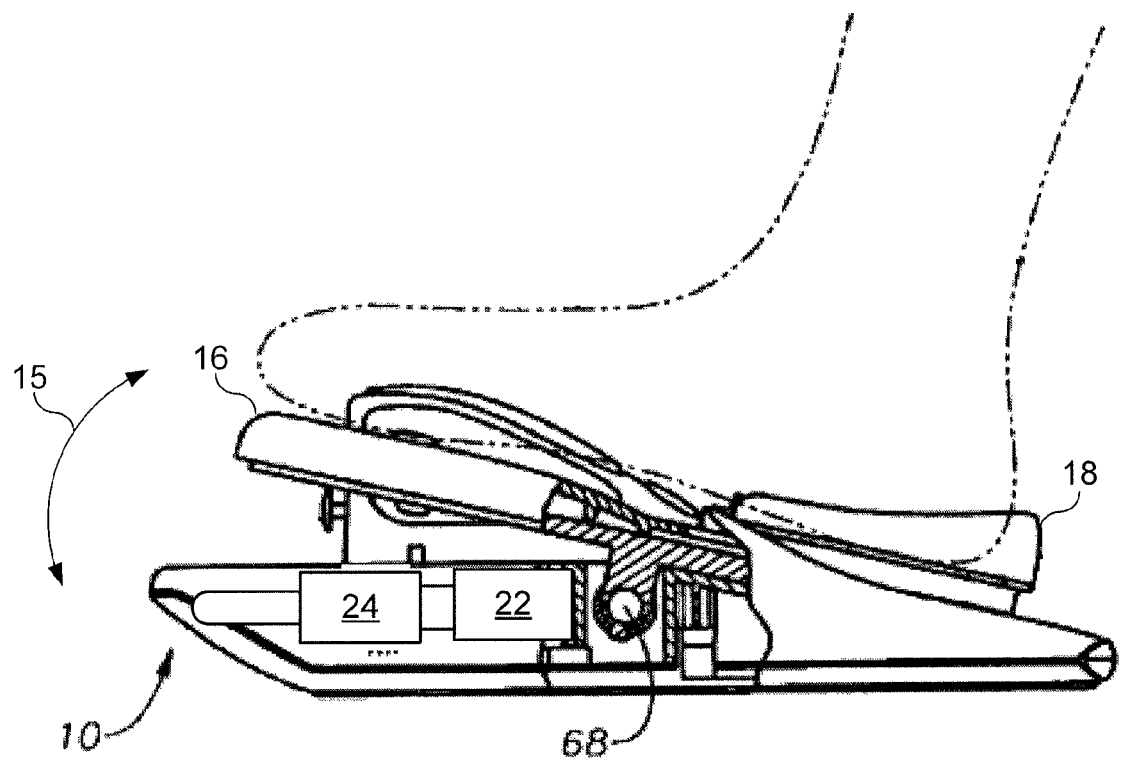
FIG. 2 provides a cross sectional view of an embodiment of a footswitch assembly in accordance with an embodiment of the present invention.

Attached to the foot pedal or tillable treadle 16 is an encoder assembly 22 as illustrated in the cross section provided by FIG. 2. Encoder assembly 22 translates the angular or pitch position of the foot pedal or treadle 16, which is tillable with respect to a horizontal plane or to a neutral or home plane, from a mechanical input based on the movement of the operator's foot into an electrical signal. Thus, the pitch 15 movement of the foot pedal or tillable treadle 16, typically in a downward direction, provides a control input. The control input is preferably a linear control input. However, when a variable high input and a constant low input is satisfactory, the neutral or home plane may provide the constant low input, and depression of the foot pedal may be used for the variable high input.

Figure 3:
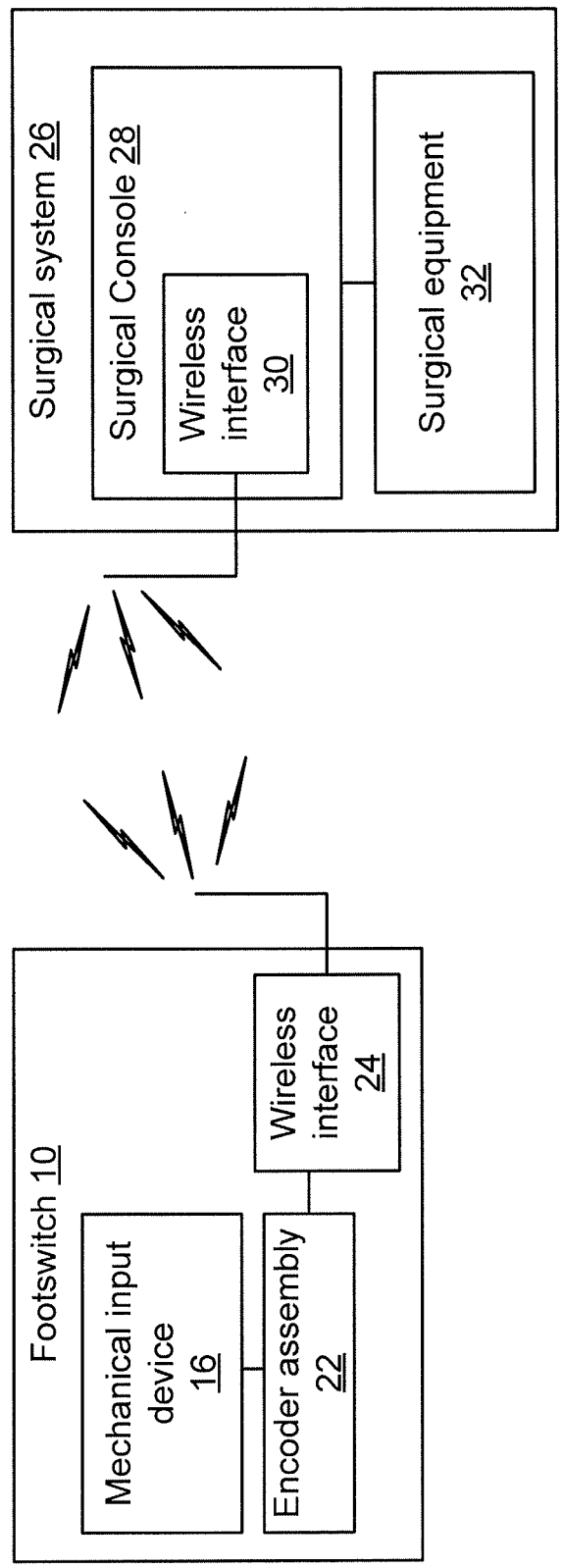
FIG. 3 provides a functional diagram that illustrates how the footswitch wirelessly couples to a surgical system in accordance with an embodiment of the present invention.

FIG. 3 provides a functional diagram that illustrates how the footswitch 10 wirelessly couples to a surgical system 26. Footswitch 10 contains a mechanical input device such as pedal 16 that couples to encoder assembly 22 in order to produce a control signal that is provided to wireless interface 24. Wireless interface 24 is operable to establish a wireless communication pathway between footswitch 10 and surgical system 26. Specifically, wireless interface 24 communicatively couples to wireless interface 30 of surgical console 28. Thus, the control signal(s) produced by encoder assembly 22 are able to be communicated to surgical console 28 via the wireless pathway. Surgical console 28 is operable to direct surgical equipment 32 based on the control signal(s) that are wirelessly relayed from the footswitch to the surgical console.

Figure 4:
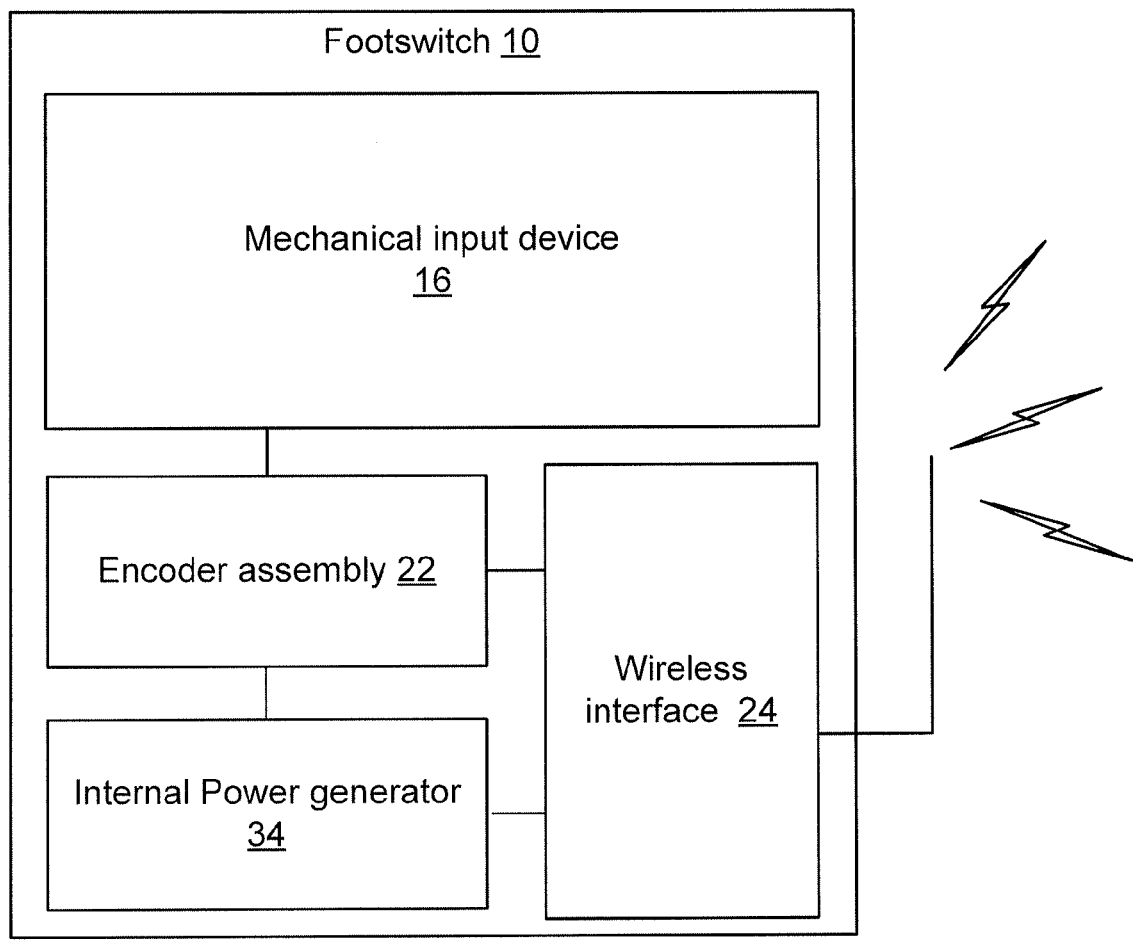
FIG. 4 depicts an embodiment of a footswitch assembly in accordance with an embodiment of the present invention.

FIG. 4 illustrates an additional embodiment of footswitch 10. As previously stated, footswitch 10 includes a mechanical input device such as pedal 16 that couples to encoder assembly 22 in order to provide a control signal to a surgical console 28 via a wireless communication pathway established by wireless interface 24. The embodiment of FIG. 4 further includes an internal power generator 34 operable to translate movement of footswitch 10 into stored energy operable to be used to power and operate the encoder assembly 22, wireless interface 24, and other components within footswitch 10.

Internal power generator 34 may both generate and store energy with which to operate footswitch 10. This may eliminate potential failure of the footswitch 10 during a procedure and overcome the need to replace batteries within the footswitch 10. There are many different ways to derive power from the movement of the surgical footswitch 10. These include, but should not be limited to, the piezoelectric effect, inductive power generation, the compression storage of compressed fluids such as air, mechanical flywheels, or other like means known to those having skill in the art. For example, when the piezoelectric effect is used to generate and store electrical energy, the mechanical energy provided by the operator to depress the pedal may compress a piezoelectric material that generates a voltage based on the mechanical energy exerted on the piezoelectric material. This electrical energy may then be stored within a capacitor or rechargeable battery in order to provide a power reserve within the footswitch. In another embodiment, the internal power generator may use inductive power generation wherein movement of the footswitch produces results in relative motion between an internal magnet and series of coils in order to charge a capacitor or rechargeable battery. Energy may also be stored in the form of mechanical energy wherein the pedal is used to spin a flywheel, which in essence is a mechanical battery. Flywheels store energy mechanically in the form of kinetic energy. Alternatively, air or other fluids can be compressed and stored and then this compressed air may be used to generate energy to power footswitch 10. These are just examples of how internal power generator 34 may generate and store energy within the footswitch.

A microprocessor or control circuit within the footswitch 10 may prompt the operator to charge the footswitch should the stored energy within internal power generator 34 fall below a pre-determined level. Alternatively, the surgical console 28 may direct the operator to charge the footswitch 10 should the stored energy fall below a pre-determined level. An indicator, such as a green LED on the footswitch 10, could indicate that the footswitch 10 is powered and ready for use.

The microprocessor or control circuit may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The memory coupled to the microprocessor or control circuit may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the microprocessor or control circuit implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The memory stores, and the microprocessor or control circuit executes, operational instructions corresponding to at least some of the steps and/or functions illustrated and described in association with FIG. 7.

The ability to power the footswitch 10 based on motion of the footswitch 10 or the mechanical motion provided by the operator eliminates the need for batteries, but more importantly it prompts the operator to recharge the footswitch 10 prior to the power falling below a pre-determined level. This helps to ensure conditions where communications between the footswitch 10 and a surgical console 28 are interrupted by power failures in the footswitch 10 that can result in improper control signals that have the potential to injure a patient. Additionally, guidelines or processes may be established and implemented by the microprocessor or control circuit such that should the wireless communications between the footswitch 10 and surgical console 28 fail, the surgical equipment returns to a pre-determined position or mode of operation in order to prevent potential injury of a patient.

Returning to FIG. 1, footswitch assembly 10 may provide additional proportional control inputs utilizing heel cup assembly 18 which enable an arcuate movement. As shown in the drawing FIGs., the heel cup assembly 18 is positioned at the rear portion of the footswitch 10 to engage the heel of the operator. The heel cup assembly 18 allows the operator to rotate the heel cup assembly 18 through an arcuate path while the operator's heel effectively remains in the same spot with respect to the footswitch assembly 10. This angular position mechanical input to a potentiometer 68 produces an electrical signal received by encoder assembly 22. This electrical signal may be an additional control signal from the footswitch 10 to the surgical system 26. This control signal may be either linear or non-linear.

To further enhance operator control, a simple on/off switch, well known to those of ordinary skill in the art, may be included in the heel cup assembly 18 to activate the signal output from the potentiometer 68. Alternatively, such on/off switches could also be used to prevent inadvertent activation of the side switches 20. Such an on/off switch may be a slide switch moving along a linear path within the heel cup assembly 18, as is designated by the arrow marked 'A' illustrated in FIG. 1.

Figure 5:
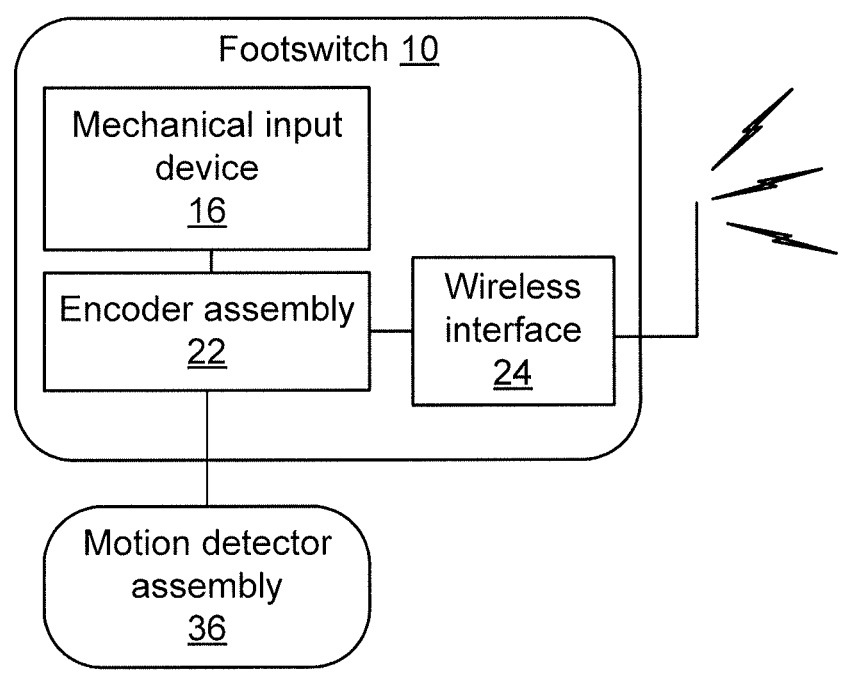
FIG. 5 illustrates another embodiment of a footswitch in accordance with an embodiment of the present invention having extended capabilities.

FIG. 5 illustrates another embodiment of footswitch 10 having extend the capabilities. Specifically, motion detector assembly 36, which may be powered by a cable or internal battery, or self-powered as discussed previously with respect to internal power generator 34, within footswitch 10 may be worn by an operator. Motion detector assembly 36 transmits motion information to the surgical footswitch 10. The surgical footswitch 10 receiving the motion information may produce additional control signal(s) based on the received information. The motion detector assembly 36 may be tethered and physically connected to footswitch 10 or wirelessly coupled to footswitch 10.

The operator may wear motion detector assembly 36 on any desired body part such as the knee, foot, arm, waist, head, fingers, shoulder, etc. Specific embodiments may prefer to wear the motion detector assembly 36 on the knee. Motion detector assembly 36 transmits position information, which may take the form of relative position information with respect to footswitch 10, to the surgical footswitch 10. This information may then be passed to a system counsel and may be used as a one, two, or three dimensional linear switch. Motion detector assembly 36, in combination with footswitch 10, enhances the control capability up to four independent dimensions.

The localization of the motion detector assembly 36 may be performed through many distinct methods. For example, acceleration sensors may be incorporated within the motion detector assembly 36 wherein the acceleration of the motion detector assembly 36 may be integrated over time to provide motion information. Another example may use radio triangulation through multiple received signals emitted within the surgical theater. This is a passive means of determining the motion information associated with the motion detector assembly 36. Alternatively, a radio frequency emitter within the motion detector assembly 36 may produce signals that are received by various receivers coupled to either the surgical footswitch 10 or surgical console 28 wherein the footswitch 10 or console 28 is operable to process this information to produce both motion information associated with the motion detector assembly 36 and a control signal resulting from the processing of the motion information.

Figure 6:
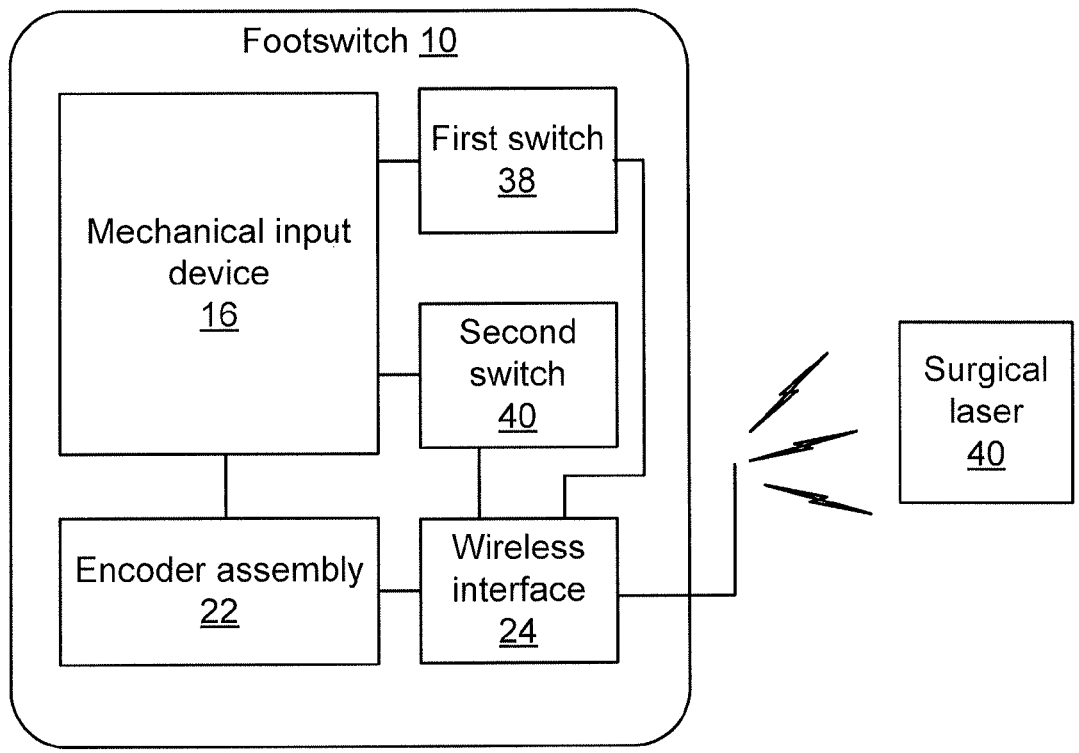
FIG. 6 provides a functional diagram of another embodiment of a surgical footswitch in accordance with an embodiment of the present invention.

FIG. 6 provides a functional diagram of another embodiment of a surgical footswitch 10. Here surgical footswitch 10 includes a mechanical input device, such as pedal 16, an encoder assembly 22 and a wireless interface 24. This embodiment further includes two switches that mechanically couple to the mechanical input device 16, first switch 38 and second switch 40. First switch 38 activates a first control signal as pedal 16 orients past a first determined point. When first switch 38 is activated, a first control signal is produced that is operable to initialize, for example, surgical laser 42 within the surgical system 26. This first switch 38 may be activated when the pedal 16 is initially depressed. The second switch 40 produces a second control signal offset in time from the first control signal produced by the activation of first switch 38. For example, second switch 40 may be activated as pedal 16 nears the end of its angular motion; i.e., when the pedal 16 is fully depressed. This second control signal may direct the firing of surgical laser 42.

The trigger time between the activation of first switch 38 and second switch 40 allows the stress on surgical laser 42 to be reduced as surgical laser 42 may not be ramped to power. The trigger time between the activation of first switch 38 and second switch 40 allows surgical laser 42 to "slowly" warm up before firing. In one embodiment, the trigger time between the activation of the two switches 38/40 is between about 100 milliseconds and 300 milliseconds. The actual time may depend on the foot speed of the operator. This allows surgical laser 42 to be slowly ramped to power over a span of about 100 milliseconds to about 300 milliseconds. This is particularly useful as certain lasers known to those having skill in art cannot be turned on in less than 50 milliseconds. The reduced stress associated with firing surgical laser 42 will result in an improved surgical laser 42 performance and reliability. Although footswitch 10 is illustrated in this embodiment as establishing a wireless communication pathway between the footswitch 10 and surgical laser 42, footswitch 10 may also physically couple to the control circuits associated with initializing and firing laser surgical 42.

Figure 7:
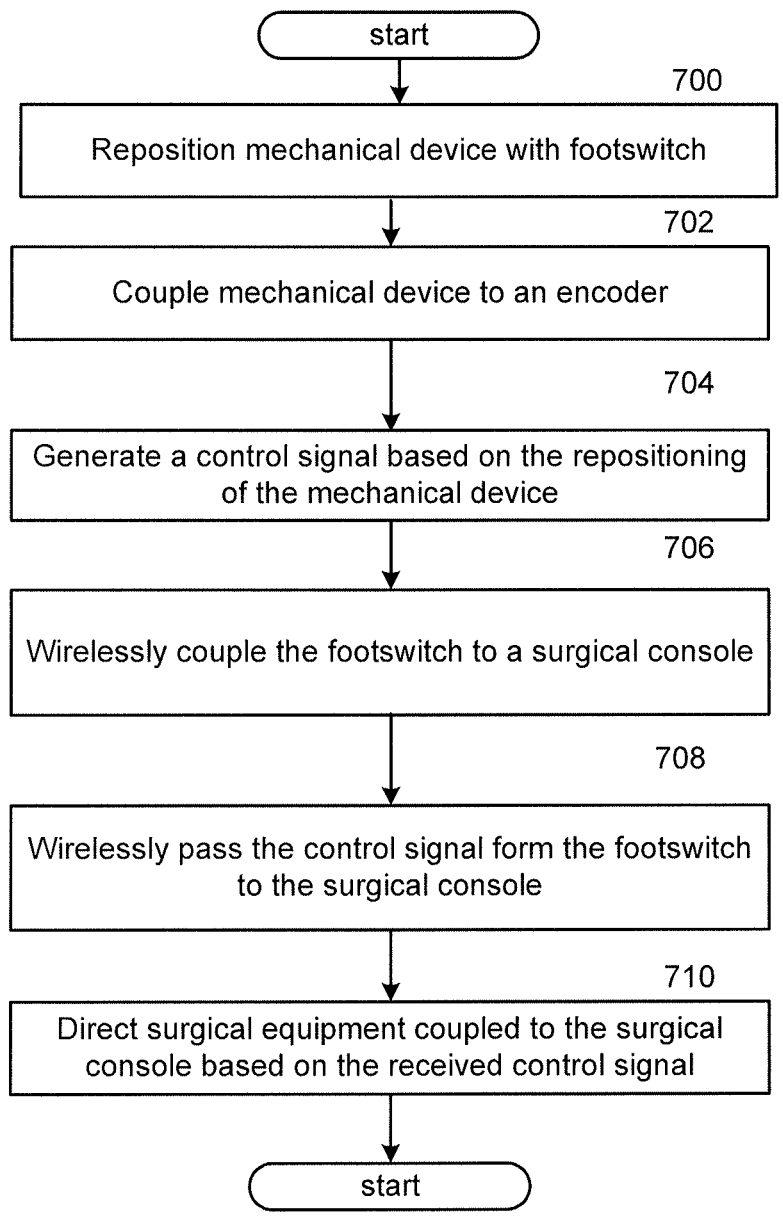
FIG. 7 provides a logic flow diagram illustrating an embodiment of a method of controlling surgical equipment in accordance with the present invention.

FIG. 7 provides a logic flow diagram illustrating a method of controlling surgical equipment in accordance with embodiments of the present invention. This method involves repositioning a mechanical device within, for example, a footswitch 10 at step 700. Footswitch 10 may be powered by an internal power generator operable to translate footswitch movement into stored energy. This allows footswitch 10 to be self powered and eliminates the need to physically couple footswitch 10 to a surgical console 28 or to a power supply. Additionally, this may eliminate the potential hazards associated with power failures within footswitch 10 during a medical procedure. The repositioning of the pedal within the surgical footswitch 10 may serve two purposes. First, it may provide mechanical energy which may be translated and stored as energy to operate the footswitch. Additionally, control signals may be generated based on the motion and positioning of the pedal. Additional switches or mechanical assemblies within footswitch 10 may also receive mechanical input that can be translated into control signals.

The pedal or mechanical device couples to an encoder at step 702. This allows the encoder to generate control signal(s) based on the repositioning of the mechanical device or pedal at step 704. The footswitch 10 wirelessly couples to the surgical console at step 706. This wireless coupling facilitates the transfer of data and other information between footswitch 10 and surgical console 28. At step 708, the control signal from footswitch 10 is passed wirelessly to surgical console 28. Surgical console 28, at step 710, is operable to direct surgical equipment coupled to console 28 based on the received control signals.

In the embodiments where footswitch 10 comprises an internal power generator 34, internal power generator 34 translates footswitch 10 movement into stored energy using processes such as an inductive power generation, piezoelectric power generation, or other like processes known to those skilled in the art. This can eliminate potential hazards associated with power failures within the footswitch that can result in unexpected control signals that produce potentially hazardous situations during surgery that could endanger a patient. A wireless coupling between footswitch 10 and surgical console 28 may be monitored wherein a communication failure may result in a processor or control circuit within surgical console 28 directing the surgical equipment to a safe condition in order to avoid potential harm to a patient.

In summary, the present invention provides a surgical footswitch 10 that comprises a base, a pedal 16, an encoder assembly 22, a wireless interface 24, and an internal power generator 34. The pedal 16 mounts upon the base and can pivot. The encoder assembly 22 couples to pedal 16. As pedal 16 pivots, the encoder assembly 22 translates the mechanical signal of pedal 16 into a control signal based on the pedal's position and/or orientation. The wireless interface 24 couples to the encoder assembly 22 to receive the control signal. The wireless interface 24 also couples surgical footswitch 10 to surgical console 28 operable to control and direct surgical equipment 32. The wireless interface 24 passes the control signal from the encoder assembly 22 to the surgical console 28, which then directs the surgical equipment 32 based on the control signal. This wireless interface 24 eliminates the tangle of wires or tethers common in the prior art and which may be a hazard in the surgical theater. The internal power generator 34 translates footswitch 10 movement into stored energy to eliminate potential failures of the footswitch 10 during a procedure and thus overcome the need to replace batteries within footswitch 10.

Other embodiments of this invention may extend the capability of surgical footswitch 10 with a motion detector assembly 36 that may be worn by a user. Motion detector assembly 36 can transmit motion information to surgical footswitch 10. The encoder assembly 22 may then generate additional control signals based on the received motion information.

Finally, other embodiments of this invention can comprise a dual switch surgical footswitch 10 operable to ramp and fire surgical laser 42. First switch 38 couples to pedal 16 and is activated as pedal 16 orients past a first predetermined point as pedal 16 is initially depressed. When first switch 38 is activated, a first control signal initializes surgical laser 42 within surgical system 26. A second switch 40 also operably couples to pedal 16 and is activated when pedal 16 orients past a second predetermined point. This second control signal directs the firing of ramped surgical laser 42. The trigger time between the activation of first switch 38 and second switch 40 allows stress on surgical laser 42 to be relieved by allowing surgical laser 42 to be ramped to power.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention is described in detail, it should be understood that various changes, substitutions and alterations can be made hereto without departing from the spirit and scope of the invention as described by the appended claims.

What is claimed is:

1. A method of controlling surgical equipment, comprising:
   repositioning a pedal within a surgical footswitch;
   coupling the pedal to an encoder, wherein the encoder is operable to generate a control signal based on repositioning of the pedal;
   wirelessly coupling a surgical footswitch to a surgical console;
   wirelessly providing control signals to the surgical console;

directing the surgical equipment with the surgical console and based on the control signal;
mounting a motion detector assembly on a user;
communicatively coupling the motion detector to the surgical footswitch;
transmitting motion information from the motion detector to the surgical footswitch, wherein the encoder is operable to generate a second control signal based on motion information; and
directing the surgical equipment with the surgical console and based on the second control signal.

2. The method of claim 1, further comprising powering the surgical footswitch with an internal power generator operable to translate footswitch movement into stored energy.

3. The method of claim 2, wherein the internal power generator comprises an inductive power generator or piezoelectrical power generator.

4. The method of claim 1, wherein the motion detector assembly and surgical footswitch are wirelessly coupled.

5. A method of firing a surgical laser with a dual switch surgical footswitch, comprising:
   pivoting a pedal about a plane associated with a base of the surgical footswitch;
   activating a first switch to generate a first control signal as the pedal orients past a first predetermined point;
   initializing the surgical laser when the first switch is activated;
   activating a second switch to generate a second control signal as the pedal orients past a second predetermined point; and
   firing the surgical laser when the second switch is activated.

6. The method of claim 5, further comprising:
   coupling the pedal to an encoder, wherein the encoder is operable to generate a third control signal based on repositioning of the pedal;
   coupling a surgical footswitch to a surgical console;
   wirelessly providing control signals to the surgical console; and
   directing the surgical equipment with the surgical console and based on the control signals.

7. The method of claim 5, wherein a trigger time between activation of the first switch and second switch is between about 100 ms and 300 ms.

8. The method of claim 5, wherein initializing the surgical laser comprises ramping the laser to power.

9. The method of claim 1, wherein the surgical console directs the surgical equipment to a predetermined state when wireless communications between the surgical footswitch and surgical console are interrupted.

* * * * *